United States Patent
Ono (10) Patent No.: US 7,010,090 B2
(45) Date of Patent: Mar. 7, 2006

(54) X-RAY DIAGNOSIS APPARATUS WITH A FUNCTION OF X-RAY FLUOROSCOPY

(75) Inventor: Masahiko Ono, Tochigi-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/345,179

(22) Filed: Jan. 16, 2003

(65) Prior Publication Data

US 2004/0141582 A1    Jul. 22, 2004

(51) Int. Cl.
*H05G 1/64* (2006.01)

(52) U.S. Cl. ..................... 378/98.7; 378/106
(58) Field of Classification Search ............. 378/98.7, 378/101, 106, 108, 109–112
See application file for complete search history.

(56) References Cited

U.S. PATENT DOCUMENTS

| | | | | |
|---|---|---|---|---|
| 5,003,572 A | * | 3/1991 | Meccariello et al. | 378/98.7 |
| 5,652,777 A | * | 7/1997 | Nagai et al. | 378/98.2 |
| 5,949,811 A | * | 9/1999 | Baba et al. | 378/108 |
| 5,966,425 A | * | 10/1999 | Beland | 378/108 |
| 6,233,310 B1 | * | 5/2001 | Relihan et al. | 378/108 |
| 6,496,563 B1 | * | 12/2002 | Bacon | 378/101 |

FOREIGN PATENT DOCUMENTS

| | | |
|---|---|---|
| JP | 4-366598 | 12/1992 |
| JP | 5-168612 | 7/1993 |
| JP | 10-118055 | 5/1998 |
| JP | 2000-306694 | 11/2000 |

* cited by examiner

*Primary Examiner*—Craig E. Church
*Assistant Examiner*—Jurie Yun
(74) *Attorney, Agent, or Firm*—Oblon, Spivak, McClelland, Maier & Neustadt, P.C.

(57) ABSTRACT

An X-ray diagnosis apparatus and method for X-ray fluoroscopy in which the apparatus includes a generator, a detector, an integrator, a comparator, and a controller. In the apparatus and method, a first X-ray for the X-ray fluoroscopy is generated intermittently. A transmission X-ray transmitted through an object of the X-ray fluoroscopy is detected. X-ray transmission data obtained in a period of intermittent generation of the first X-ray is integrated and compared to a reference value. In response to the integrated X-ray transmission data reaching the reference value during the period of intermittent generation, intermittent generation of the first X-ray is disabled.

10 Claims, 8 Drawing Sheets

X-RAY DIAGNOSIS APPARATUS WITH A FUNCTION OF X-RAY FLUOROSCOPY

CROSS-REFERENCE TO RELATED APPLICATION

This application is related to Japanese Patent Application No. P2001-306900, filed on Oct. 2, 2001, the entire contents of which are incorporated herein by reference.

BACKGROUND OF THE INVENTION

1. Field of the Invention

The present invention relates to an X-ray diagnosis apparatus with a function of X-ray fluoroscopy and a method of X-ray fluoroscopy, wherein X-ray fluoroscopic images are produced by X-rays generated intermittently.

2. Discussion of the Background

It is known that X-ray fluoroscopic images are obtained in an X-ray diagnosis apparatus. Recently, an X-ray fluoroscopy for such images has been achieved by radiation of an X-ray towards an object, such as a patient, in a form of a plurality of intermittent pulses. Such an X-ray is hereinafter referred to as an intermittent pulse X-ray, an intermittent X-ray pulse, or just simply an X-ray pulse. An auto brightness control (ABC) is known as a conventional technique to obtain an optimal or preferable brightness of an X-ray fluoroscopic image by the intermittent pulse X-ray radiation.

Figure 1:
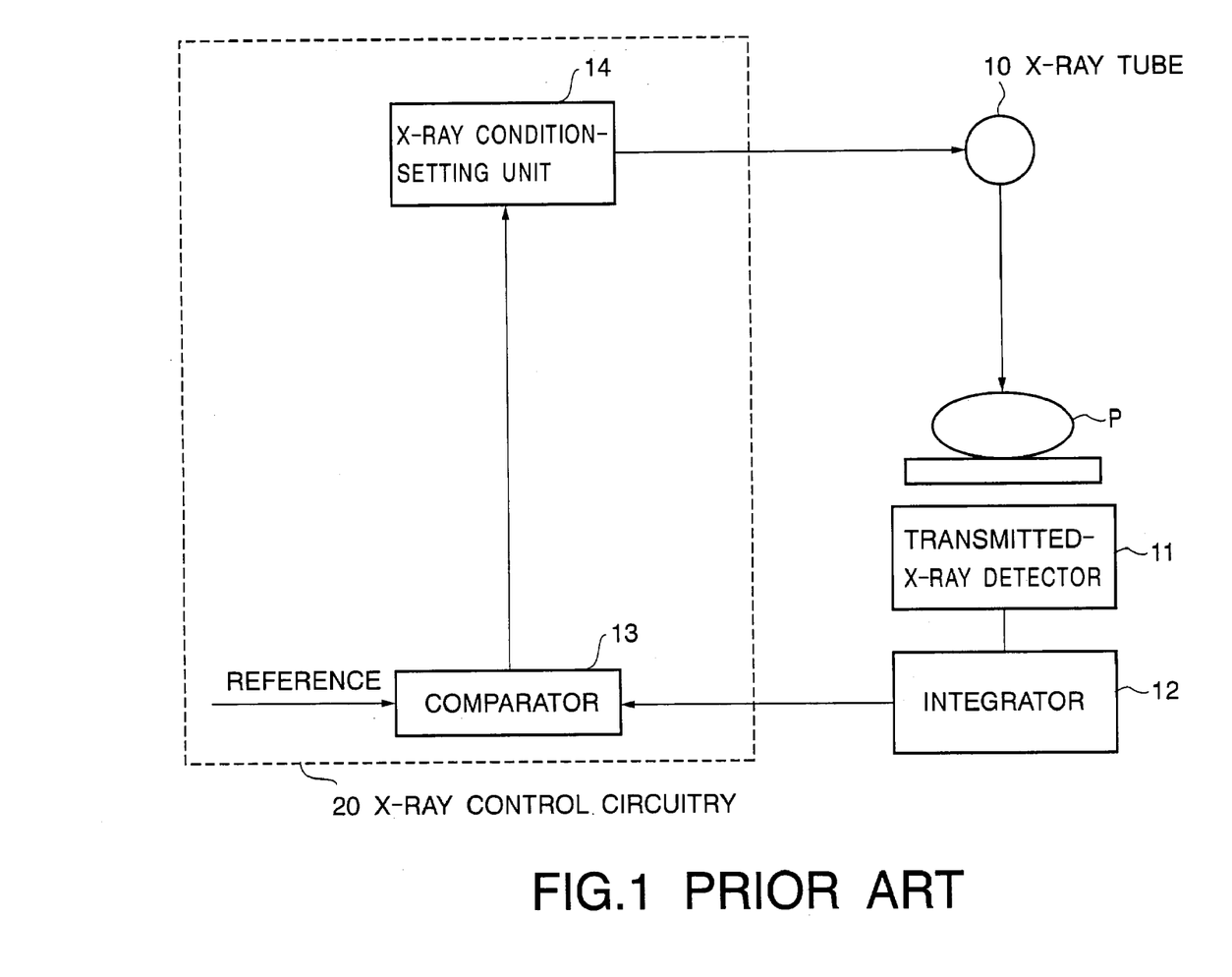
FIG. 1 is a block diagram showing an X-ray diagnosis apparatus according to a prior art.

The ABC will be explained with reference to FIGS. 1 and 2. FIG. 1 is a block diagram showing an X-ray diagnosis apparatus according to a prior art. As shown in FIG. 1, the X-ray diagnosis apparatus generally includes an X-ray tube 10, a transmitted-X-ray detector 11, an integrator 12, and an X-ray control circuitry 20. The X-ray control circuitry 20 includes a comparator 13 and an X-ray condition-setting unit 14. The X-ray tube 10 radiates an X-ray towards a patient P. The transmitted-X-ray detector 11 detects an X-ray transmitted through the patient P as a result of the X-ray radiation by the X-ray tube 10. The integrator 12 integrates detected results obtained from the transmitted-X-ray detector 11. The comparator 13 compares an integrated result obtained from the integrator 12 to a reference value. The reference value is usually determined, in advance, to represent an optimal or preferable brightness of an X-ray fluoroscopic image. The X-ray condition-setting unit 14 sets and controls X-ray conditions of the X-ray radiation by the X-ray tube 10, such as an X-ray tube voltage, an X-ray tube current, and a pulse width of the intermittent pulse X-ray, based on a comparison result obtained from the comparator 13.

Figure 2:
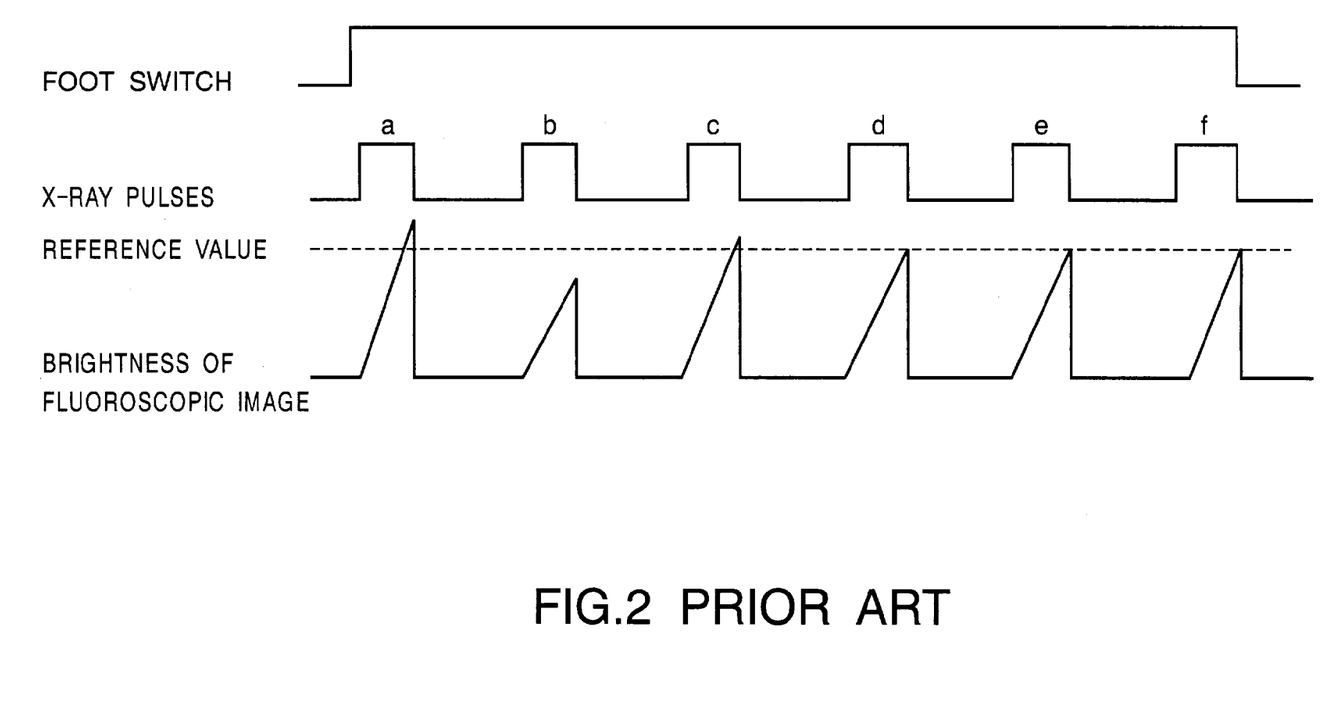
FIG. 2 is a diagram showing a conventional process of an ABC in the X-ray diagnosis apparatus according to the prior art.

FIG. 2 is a diagram showing a conventional process of the ABC in the X-ray diagnosis apparatus according to the prior art. Responsive to activation of an X-ray radiation switch (foot switch) by an operator, the X-ray radiation begins for the X-ray fluoroscopy. The X-ray radiation is made with the intermittent pulse X-ray. In such an X-ray fluoroscopy, a brightness of an X-ray fluoroscopic image is optimized in the X-ray diagnosis apparatus shown in FIG. 1.

First of all, a first X-ray pulse (a first intermittent pulse X-ray) (a) is radiated to the patient P as shown in FIG. 2. The first X-ray pulse (a) is detected in the transmitted X-ray detector 11 and integrated in the integrator 12. The integrated X-ray data which represent a brightness of an X-ray fluoroscopic image are fed back to the comparator 13. In the comparator 13, the integrated X-ray data are compared to the reference value. The comparison result is fed to the X-ray condition-setting unit 14. A condition of a next X-ray pulse is determined according to the comparison result and is set for the X-ray tube 10. The condition to be determined includes, for example, an X-ray tube voltage, an X-ray tube current, and a pulse width of the X-ray pulse. The pulse width may often be fixed while the X-ray tube voltage and the X-ray tube current are usually changed in such a determination. Under the set condition, a second X-ray pulse (a second intermittent pulse X-ray) (b) is radiated to the patient P and a similar brightness control is performed as described above. By repeating such brightness control processes several times, a brightness of an X-ray fluoroscopic image to be obtained comes close to the reference value. Since a required X-ray pulse for the predetermined optimal or preferable brightness varies in response to a body movement of the patient P (this is because a thickness of the body to be X-ray transmitted is changed as the patient moves even slightly), the detected and integrated X-ray data are compared to the reference value in succession in the following X-ray pulses, such as X-ray pulses (c), (d), (e), and (f).

In the ABC, however, requires repetition of X-ray pulses radiation to obtain the optimal or preferable brightness of an X-ray fluoroscopic image. Accordingly, it usually takes time to reach such brightness and keep it stable through images. Particularly, when X-ray pulses are radiated intermittently at a low rate (radiated less often in a predetermined unit time), it is likely to happen to take tens of seconds to reach the optimal or preferable brightness. Further, such repeated radiation is obviously harmful to the patient P.

SUMMARY OF THE INVENTION

According to a first aspect of the present invention, there is provided an X-ray diagnosis apparatus having a generator configured to generate intermittently a first X-ray for the X-ray fluoroscopy, a detector configured to detect a transmission X-ray of the first X-ray transmitted through an object of the X-ray fluoroscopy and to output X-ray transmission data, an integrator configured to integrate the X-ray transmission data during a period of intermittent generation of the first X-ray, a comparator configured to compare integrated X-ray transmission data to a reference value, and a controller configured to disable the generator during the period of intermittent generation in response to the integrated X-ray transmission data reaching the reference value.

According to a second aspect of the present invention, there is provided a method of an X-ray fluoroscopy including generating intermittently a first X-ray for the X-ray fluoroscopy, detecting a transmission X-ray of the first X-ray transmitted through an object of the X-ray fluoroscopy, integrating X-ray transmission data obtained in a period of intermittent generation of the first X-ray, comparing an integrated X-ray transmission data obtained in the integrating step to a reference value, and disabling, during the period of intermittent generation, the intermittent generation of the first X-ray in response to the integrated X-ray transmission data reaching the reference value.

According to a third aspect of the present invention, there is provided a computer program product on which is stored a computer program for X-ray fluoroscopy, the computer program having instructions, which when executed perform steps including generating intermittently a first X-ray for the X-ray fluoroscopy, detecting a transmission X-ray of the first X-ray transmitted through an object of the X-ray fluoroscopy, integrating X-ray transmission data obtained in a period of intermittent generation of the first X-ray, comparing an integrated X-ray transmission data obtained in the integrating step to a reference value, and disabling, during the period of intermittent generation, the intermittent generation of the first X-ray in response to the integrated X-ray transmission data reaching the reference value.

BRIEF DESCRIPTION OF THE DRAWINGS

A more complete appreciation of embodiments of the present invention and many of its attendant advantages will be readily obtained by reference to the following detailed description considered in connection with the accompanying drawings, in which.

DESCRIPTION OF THE PREFERRED EMBODIMENTS

Various other objects, features and attendant advantages of the present invention will be more fully appreciated as the same becomes better understood from the following detailed description when considered in connection with the accompanying drawings in which like reference characters designate like or corresponding parts throughout the several views. In the following description of preferred embodiments of the present invention an auto exposure control (hereinafter referred to as an AEC) can be a basic technique to be used in an X-ray diagnosis apparatus, and the aforementioned ABC may further be added for a combination use with the AEC. AEC is a technique in which an X-ray tube voltage and an X-ray tube current are fixed while a pulse width of X-ray pulses (an X-ray radiation time for each X-ray pulse) is controlled (i.e. changed) in each intermittently radiated X-ray (each X-ray pulse) so as to obtain an optimal, preferable, or user-intended brightness (hereinafter referred to as an optimal brightness) of an X-ray fluoroscopic image. Here such intermittent X-ray (pulse) radiation may be defined as an X-ray (pulse) radiation in which an X-ray is continually radiated with an interval between one pulse and the next. The interval may or may not be constant since an X-ray radiation rate may be fixed, and at the same time there is a possibility of differences in the X-ray radiation time between the pulses.

(First Embodiment)

Figure 3:
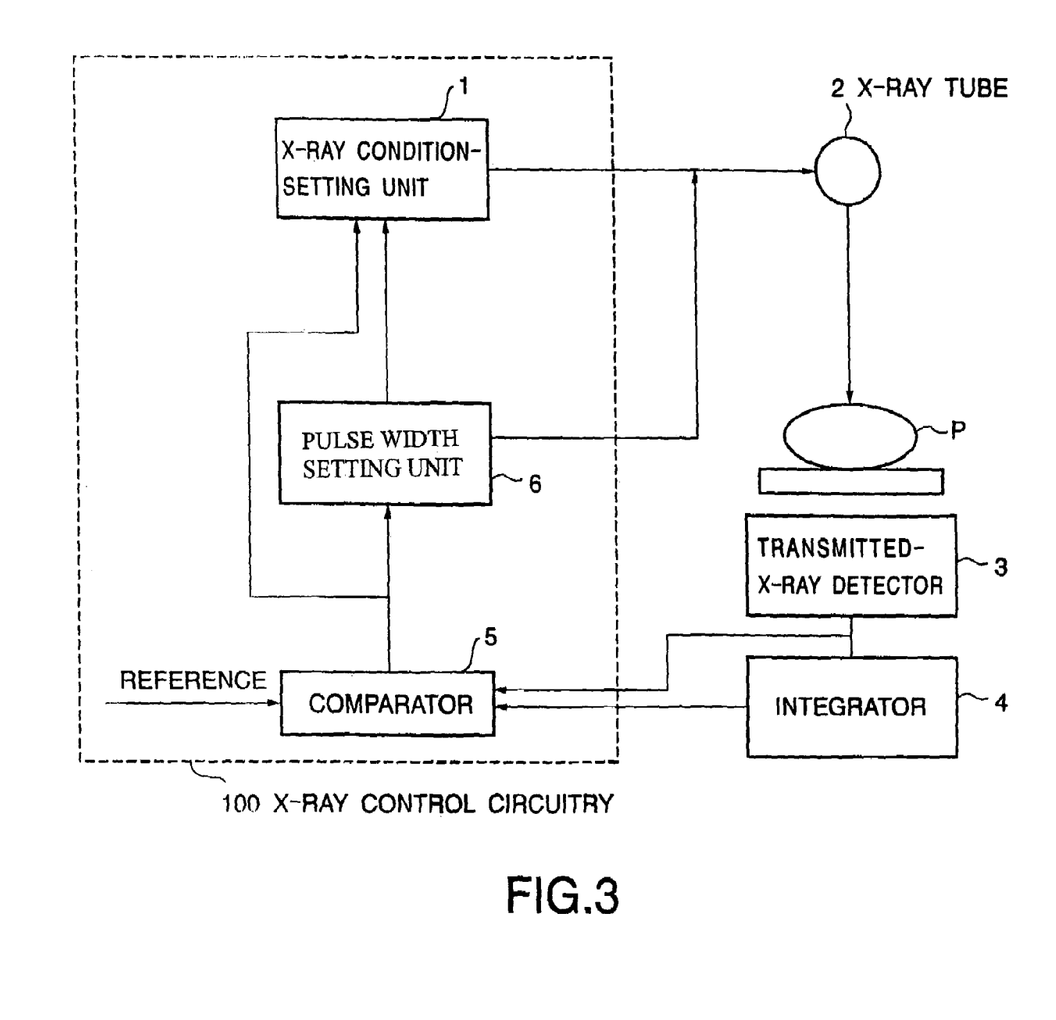
FIG. 3 is a block diagram showing an X-ray diagnosis apparatus according to the present invention.

A configuration of an X-ray diagnosis apparatus according to a first embodiment of the present invention will be explained with reference to FIG. 3. FIG. 3 is a block diagram showing the X-ray diagnosis apparatus according to the first embodiment of the present invention. Further, FIG. 4 is a diagram showing a process of the AEC in the X-ray diagnosis apparatus according to the first embodiment of the present invention.

As shown in FIG. 3, the X-ray diagnosis apparatus includes an X-ray tube 2, a transmitted-X-ray detector 3, an integrator 4, and an X-ray control circuitry 100. The X-ray control circuitry 100 includes a comparator 5, a time measurement unit 6, and an X-ray condition-setting unit 1. The X-ray tube 2 radiates an X-ray towards a patient P. The transmitted X-ray detector 3 detects an X-ray transmitted through the patient P as a result of the X-ray radiation by the X-ray tube 2. The integrator 4 integrates detected results obtained from the transmitted-X-ray detector 3. The comparator 5 compares an integrated result obtained from the integrator 4 to a reference value. The reference value is usually determined, in advance, to represent an optimal brightness of an X-ray fluoroscopic image. The time measurement unit 6 generates termination signals to control the X-ray radiation time (a width of each intermittent X-ray pulse) by the X-ray tube 2, based on a comparison result obtained from the comparator 5. The X-ray condition-setting unit 1 sets X-ray conditions of the X-ray radiation by the X-ray tube 2, such as an X-ray tube voltage and an X-ray tube current. The time measurement unit 6 may also be incorporated and implemented in the X-ray condition-setting unit 1.

Responsive to activation of an X-ray radiation switch (foot switch) by an operator, the X-ray tube 2 begins the X-ray radiation for the X-ray fluoroscopy. The X-ray radiation is made with the intermittent pulses X-ray under the X-ray tube voltage (kV) and the X-ray tube current (mA) set in advance by the X-ray condition-setting unit 1. The width (msec) of each intermittent X-ray pulse is not fixed but varies according to the control by the time measurement unit 6.

Figure 4:
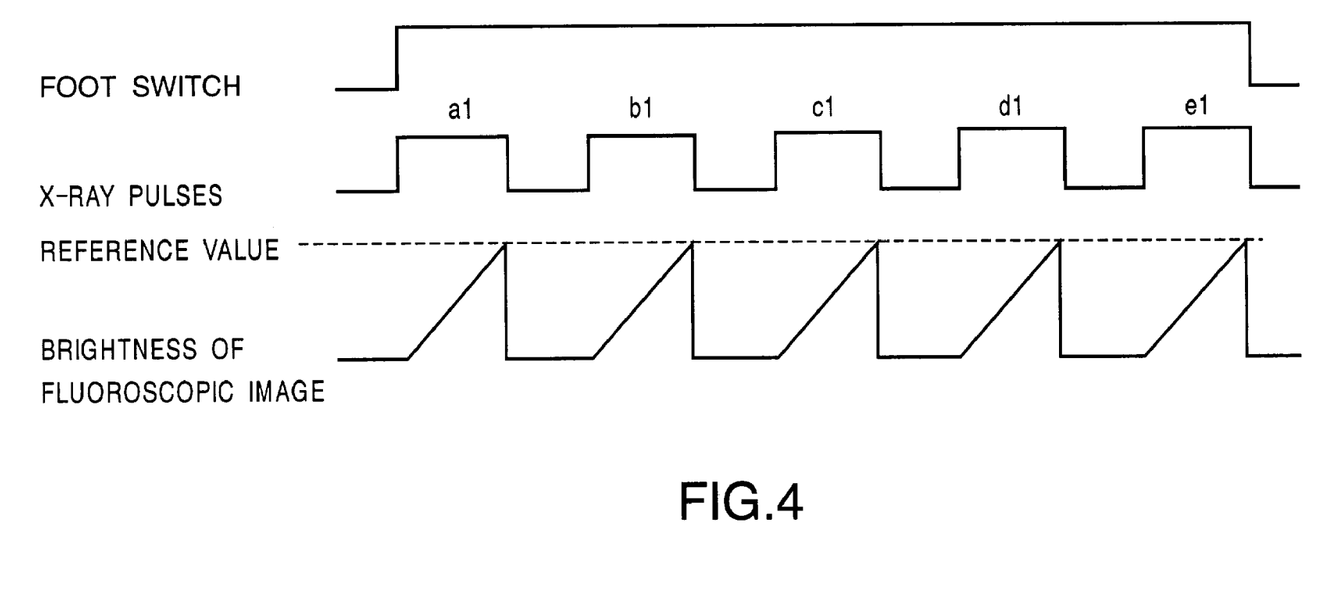
FIG. 4 is a diagram showing a process of an auto exposure control (AEC) in the X-ray diagnosis apparatus according to the present invention.

Responsive to the activation of the X-ray radiation, a first X-ray pulse (a first intermittent pulse X-ray) (a1) is radiated to the patient P as shown in FIG. 4. The first X-ray pulse (a1) is detected as a transmission X-ray in the transmitted X-ray detector 3. To be more precise, the transmission X-ray is detected in the transmitted X-ray detector 3 as a result that the first X-ray pulse (a1) is transmitted through the patient P. The transmission X-ray detected in the transmitted X-ray detector 3 is sent to the integrator 4. The integrator 4 continues to integrate the transmission X-ray and feeds the integrated transmission X-ray to the comparator 5 as transmission X-ray data at predetermined intervals. The comparator 5 compares the fed transmission X-ray data to the reference value at predetermined intervals.

As described above, the width of each intermittent X-ray pulse is not fixed but varies according to the control by the time measurement unit 6. Therefore, the radiation in the first X-ray pulse (a1) continues until terminated by the termination control by the time measurement unit 6 and, as a result, the transmission X-ray data increase as the radiation time goes by.

The comparison result by the comparator 5 is sent to the time measurement unit 6. The comparison result may, for example, be signals representing whether the transmission X-ray data have reached the reference value or not. When the time measurement unit 6 receives such signals representing that the transmission X-ray data have reached the reference value, the time measurement unit 6 sends termination signals to the X-ray tube 2 so that the X-ray tube 2 terminates its X-ray radiation. Once the X-ray radiation is terminated, the X-ray is not radiated until a time for a second X-ray pulse (b1). The AEC process described above may be repeated in each of the following X-ray pulses, such as X-ray pulses (b1), (c1), (d1), and (e1), in a similar manner. This results in producing X-ray fluoroscopic images with an optimal brightness.

Also in the following X-ray pulses if, for example, the radiation time for the first X-ray pulse (a1) is determined to be rather long, at least one of the X-ray tube voltage and the X-ray tube current may be increased or controlled to be adjusted by the X-ray condition-setting unit 1 in response to the time measurement unit 6 so that the radiation time can be shortened. Similarly, if, for example, the radiation time for the first X-ray pulse (a1) is determined to be rather short, at least one of the X-ray tube voltage and the X-ray tube current may be decreased or controlled to be adjusted by the X-ray condition-setting unit 1 in response to the time measurement unit 6 so that the radiation time can be lengthened.

In the X-ray diagnosis apparatus according to the first embodiment of the present invention, it may be possible to obtain the optimal and stable brightness of an X-ray fluoroscopic image more quickly than when the conventional ABC was applied. This technique of the present invention may be even more of an advantageous when the X-ray fluoroscopy is performed at a low rate, such as for example 2.5 frames per second (fps), 2 fps, or 1 fps, rather than at a high rate, such as for example 7.5 fps, 15 fps, or 30 fps.

(Second Embodiment)

Figure 5:
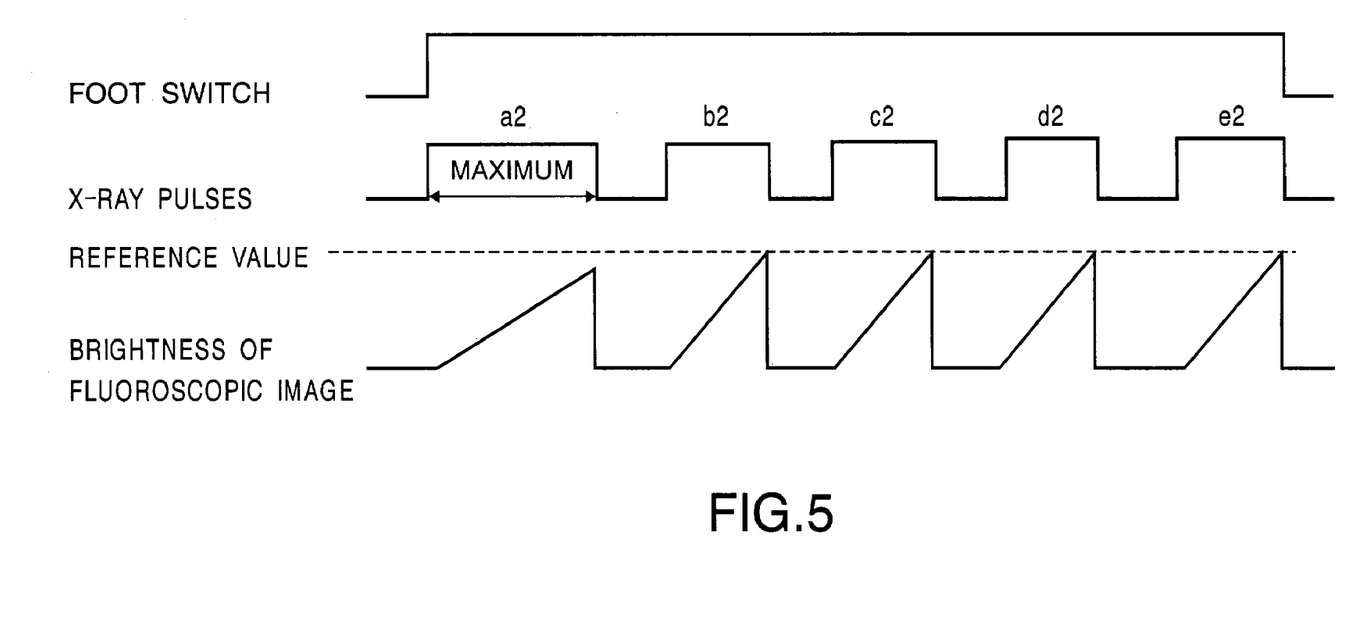
FIG. 5 is a diagram showing another process of the AEC in the X-ray diagnosis apparatus according to the present invention.
Figure 6:
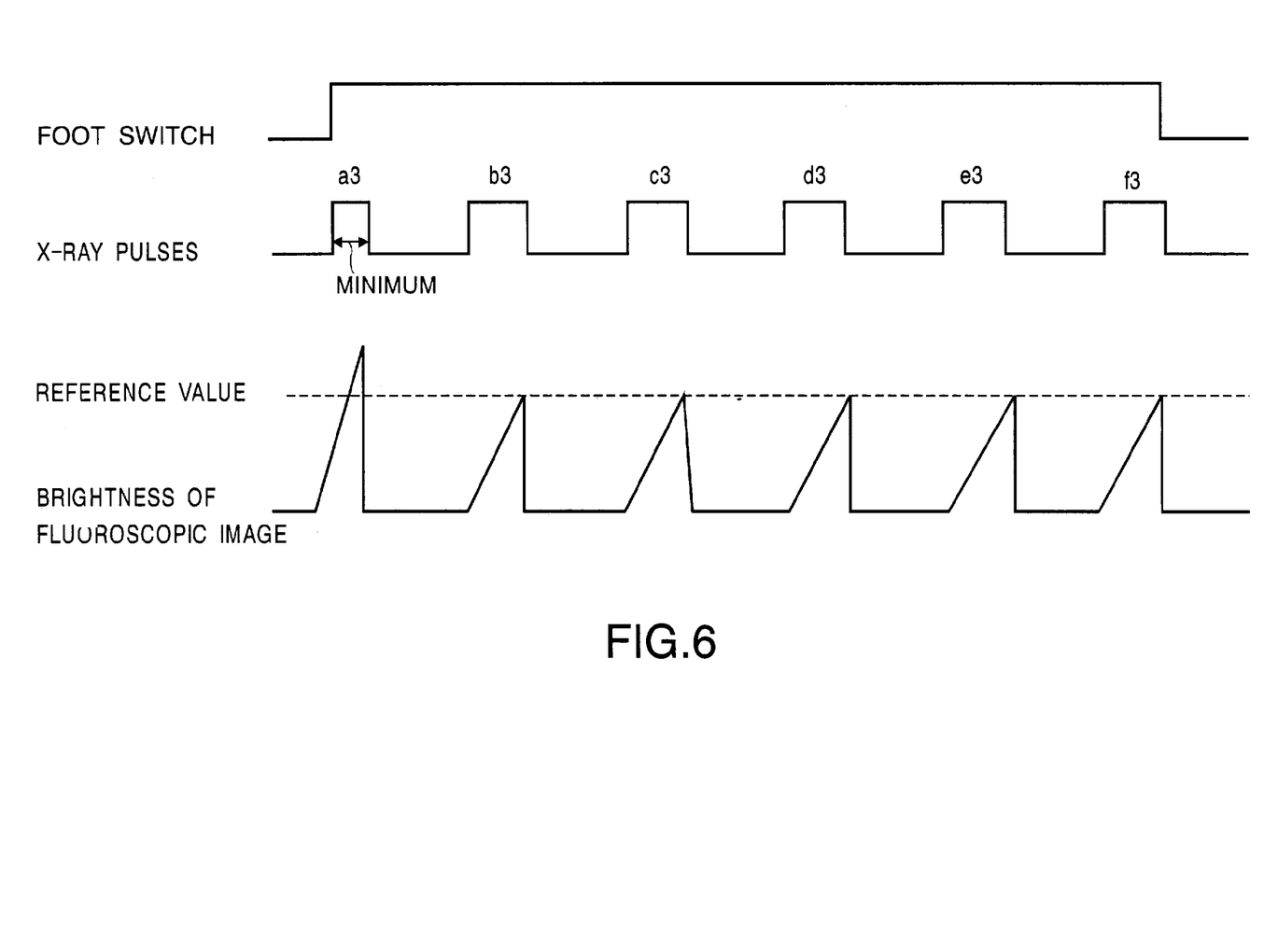
FIG. 6 is a diagram showing still another process of the AEC in the X-ray diagnosis apparatus according to the present invention.

A configuration of an X-ray diagnosis apparatus according to a second embodiment of the present invention will be explained with reference to FIG. 3 again. Further, FIG. 5 is a diagram showing another process of the AEC in the X-ray diagnosis apparatus according to the second embodiment of the present invention. Still further, FIG. 6 is a diagram showing still another process of the AEC in the X-ray diagnosis apparatus according to the second embodiment of the present invention.

The X-ray diagnosis apparatus according to the second embodiment of the present invention may include a concept of the X-ray diagnosis apparatus according to the first embodiment of the present invention. In the first embodiment of the present invention, the X-ray tube voltage (kV) and the X-ray tube current (mA) for the X-ray pulses radiated towards the patient P were determined and fixed in advance, and the radiation time (the width of each intermittent X-ray pulse) (msec) was flexibly controlled based on the X-ray transmission data fed back from the integrator 4 so as to obtain an optimal brightness of an X-ray fluoroscopic image.

In practice, however, the width of each intermittent X-ray pulse is limited in size and must be within a predetermined maximum width (an allowable maximum length of the radiation time). The maximum width may be determined from a reading time in a radiographic system including a CCD and a radiographic tube. Further, an X-ray pulse rate (the number of pulses in a predetermined unit time) can be another element to limit the maximum width since the predetermined number of pulses must be generated or kept in the predetermined unit time once the pulse rate is determined.

Accordingly, when, for example, the X-ray tube voltage and the X-ray tube current set for a first X-ray pulse (a2) are lower than needed, even if the first X-ray pulse (a2) is radiated from the X-ray tube 2 for the allowable maximum length of the X-ray pulse radiation time, transmission X-ray data integrated by the integrator 4 may happen not to reach the reference value in such a period. As mentioned before, the brightness is determined by the transmission X-ray data integrated for each X-ray pulse.

On the other hand, when, for example, the X-ray tube voltage and the X-ray tube current set for the first X-ray pulse (a2) are higher than needed, even if the first X-ray pulse (a2) is radiated from the X-ray tube 2 only for the allowable minimum length of the X-ray pulse radiation time, transmission X-ray data integrated by the integrator 4 may happen to exceed the reference value in such a period. The minimum length of the X-ray pulse radiation time may be determined by a risetime of the X-ray pulse. The risetime is required as a minimum time for the X-ray pulse.

According to the second embodiment of the present invention, when the transmission X-ray data integrated by the integrator 4 may happen not to reach the reference value in the allowable maximum length of the X-ray pulse radiation time, at least one of the X-ray tube voltage and the X-ray tube current for the next X-ray pulse radiation may be increased or controlled to be adjusted by the X-ray condition-setting unit 1 so that the transmission X-ray data reach the reference value within the allowable maximum length of the X-ray pulse radiation time. On the other hand, similarly, when the transmission X-ray data integrated by the integrator 4 may happen to exceed the reference value in the allowable minimum length of the X-ray pulse radiation time, at least one of the X-ray tube voltage and the X-ray tube current for the next X-ray pulse radiation may be decreased or controlled to be adjusted by the X-ray condition-setting unit 1 so that the transmission X-ray data do not exceed but reach the reference value within the allowable maximum length of the X-ray pulse radiation time. Such controls of the voltage and/or the current may automatically be performed in the X-ray condition-setting unit 1.

As shown in FIG. 3, the X-ray diagnosis apparatus includes an X-ray tube 2, a transmitted X-ray detector 3, an integrator 4, and an X-ray control circuitry 100. The X-ray control circuitry 100 includes a comparator 5, a time measurement unit 6, and an X-ray condition-setting unit 1. The X-ray tube 2 radiates an X-ray towards a patient P. The transmitted X-ray detector 3 detects an X-ray transmitted through the patient P as a result of the X-ray radiation by the X-ray tube 2. The integrator 4 integrates detected results obtained from the transmitted X-ray detector 3. The comparator 5 compares an integrated result obtained from the integrator 4 to a reference value. The reference value is usually determined, in advance, to represent an optimal brightness of an X-ray fluoroscopic image. The time measurement unit 6 generates termination signals to control the X-ray radiation time (a width of each intermittent X-ray pulse) by the X-ray tube 2, based on a comparison result obtained from the comparator 5. The X-ray condition-setting unit 1 sets X-ray conditions of the X-ray radiation by the X-ray tube 2, such as an X-ray tube voltage and an X-ray tube current. The time measurement unit 6 may also be incorporated and implemented in the X-ray condition-setting unit 1.

Responsive to activation of an X-ray radiation switch (foot switch) by an operator, the X-ray tube 2 begins the X-ray radiation for the X-ray fluoroscopy. The X-ray radiation is made with the intermittent pulses X-ray under the X-ray tube voltage (kV) and the X-ray tube current (mA) set in advance by the X-ray condition-setting unit 1. The width (msec) of each intermittent X-ray pulse is not fixed but varies according to the control by the time measurement unit 6.

Responsive to the activation of the X-ray radiation, a first X-ray pulse (a first intermittent pulse X-ray) (a2)/(a3) is radiated to the patient P as shown in respective FIG. 5 and 6. The first X-ray pulse (a2)/(a3) is detected as a transmission X-ray in the transmitted-X-ray detector 3. To be more precise, the transmission X-ray is detected in the transmitted-X-ray detector 3 as a result that the first X-ray pulse (a2)/(a3) is transmitted through the patient P. The transmission X-ray detected in the transmitted X-ray detector 3 is sent to the integrator 4. The integrator 4 continues to integrate the transmission X-ray and feeds the integrated transmission X-ray to the comparator 5 as transmission X-ray data at predetermined intervals. The comparator 5 compares the fed transmission X-ray data to the reference value at predetermined intervals.

As described above, the width of each intermittent X-ray pulse is not fixed but varies according to the control by the time measurement unit 6. Therefore, the radiation in the first X-ray pulse (a2)/(a3) continues until terminated by the termination control by the time measurement unit 6, and, as a result, the transmission X-ray data increase as the radiation time goes by.

In the case of FIG. 5, the comparison result by the comparator 5 is sent to the time measurement unit 6. The comparison result may, for example, be signals representing whether the transmission X-ray data have reached the reference value or not. When the time measurement unit 6 receives such signals representing that the transmission X-ray data have not reached the reference value in spite of the elapse of the allowable maximum length of the X-ray pulse radiation time, such signals are transferred to the X-ray condition-setting unit 1. Such signals may alternatively be sent to the X-ray condition-setting unit 1 directly from the comparator 5. The X-ray condition-setting unit 1 increases or controls to adjust at least one of the X-ray tube voltage and the X-ray tube current for the second X-ray pulse (b2) so that the transmission X-ray data reach the reference value within the allowable maximum length of the X-ray pulse radiation time. Accordingly, the second X-ray pulse (b2) is radiated with a newly set condition including an increased or controlled X-ray tube voltage and/or an increased or controlled X-ray tube current.

Similar to the first X-ray pulse (a2), the radiation in the second X-ray pulse (b2) continues until terminated by the termination control by the time measurement unit 6 and, as a result, the transmission X-ray data increase as the radiation time goes by. The comparison result by the comparator 5 is sent to the time measurement unit 6. When the time measurement unit 6 receives signals representing that the transmission X-ray data have reached the reference value, the time measurement unit 6 sends termination signals to the X-ray tube 2 so that the X-ray tube 2 terminates its X-ray radiation. Once the X-ray radiation is terminated, the X-ray is not radiated until a time for a third X-ray pulse (c2). The AEC process described above may be repeated in each of the following X-ray pulses, such as X-ray pulses (c2), (d2), and (e2), in a similar manner. This results in producing X-ray fluoroscopic images with an optimal brightness.

On the other hand, contrary to the above case, in the case of FIG. 6, if the time measurement unit 6 receives signals representing that the transmission X-ray data have exceeded the reference value only in the allowable minimum length of the X-ray pulse radiation time, such signals are transferred to the X-ray condition-setting unit 1. Such signals may alternatively be sent to the X-ray condition-setting unit 1 directly from the comparator 5. The X-ray condition-setting unit 1 decreases or controls to adjust at least one of the X-ray tube voltage and the X-ray tube current for the second X-ray pulse (b3) so that the transmission X-ray data do not exceed but reach the reference value within the allowable maximum length of the X-ray pulse radiation time. Accordingly, the second X-ray pulse (b3) is radiated with a newly set condition including a decreased or controlled X-ray tube voltage and/or a decreased or controlled X-ray tube current.

Similar to the first X-ray pulse (a3), the radiation in the second X-ray pulse (b3) continues until terminated by the termination control by the time measurement unit 6 and, as a result, the transmission X-ray data increase as the radiation time goes by. The comparison result by the comparator 5 is sent to the time measurement unit 6. When the time measurement unit 6 receives signals representing that the transmission X-ray data have reached the reference value, the time measurement unit 6 sends termination signals to the X-ray tube 2 so that the X-ray tube 2 terminates its X-ray radiation. Once the X-ray radiation is terminated, the X-ray is not radiated until a time for a third X-ray pulse (c3). The AEC process described above may be repeated in each of the following X-ray pulses, such as X-ray pulses (c3), (d3), (e3), and (f3), in a similar manner. This results in producing X-ray fluoroscopic images with an optimal brightness.

In the X-ray diagnosis apparatus according to the second embodiment of the present invention, it may be possible to obtain the optimal and maybe stable brightness of an X-ray fluoroscopic image more quickly than when the conventional ABC was applied. This technique of the present invention may be even more advantageous when the X-ray fluoroscopy is performed at a low rate, such as for example 2.5 frames per second (fps), 2 fps, or 1 fps, rather than at a high rate, such as for example 7.5 fps, 15 fps, or 30 fps.

Further, the second embodiment of the present invention has been described about a case in which the transmission X-ray data are approximated to the reference value in the radiation of the second X-ray pulse (b2)/(b3). If, however, a similar problem mentioned in this embodiment has happened in the radiation of the second X-ray pulse (b2) 1 (b3), at least one of the X-ray tube voltage and the X-ray tube current are controlled (or changed) again for the third X-ray pulse (c2)/(c3) or the following X-ray pulse until the transmission X-ray data are approximated to the reference value.

(Third Embodiment)

Figure 7:
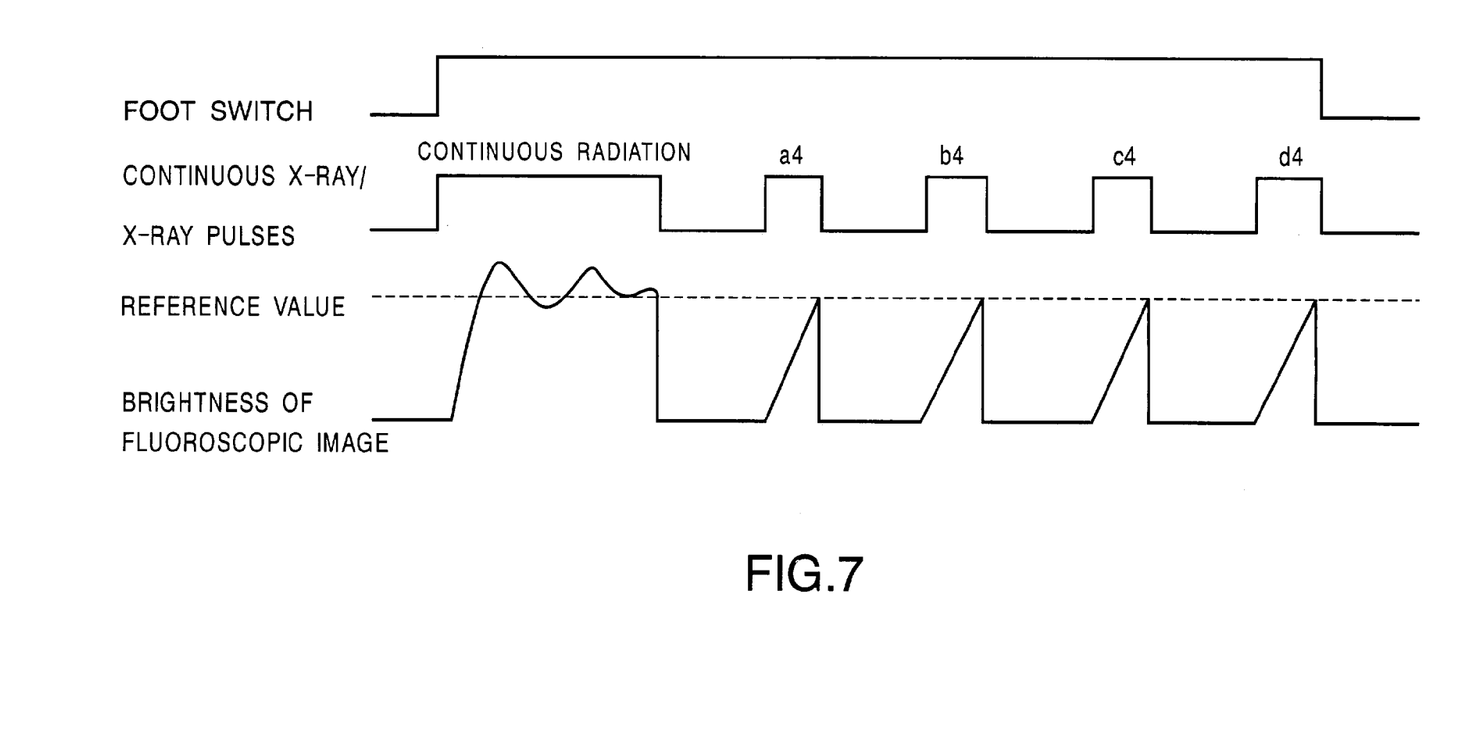
FIG. 7 is a diagram showing a process for obtaining an optimal or preferable brightness of an X-ray fluoroscopic image in the X-ray diagnosis apparatus according to the present invention.

A configuration of an X-ray diagnosis apparatus according to a third embodiment of the present invention will be explained with reference to FIG. 3 again. Further, FIG. 7 is a diagram showing a process for obtaining an optimal brightness of an X-ray fluoroscopic image in the X-ray diagnosis apparatus according to the third embodiment of the present invention.

In the X-ray diagnosis apparatus according to the third embodiment of the present invention, a continuous (or continual) X-ray fluoroscopy is implemented in advance of the AEC, such as, but not limited to, those described in the first and the second embodiments of the present invention. Accordingly, an initial X-ray tube voltage and/or an initial X-ray tube current for the AEC may be determined based on a result of the advance continuous X-ray fluoroscopy. The continuous X-ray fluoroscopy may be performed with either the conventional ABC or a technique using a concept of the AEC. The third embodiment of the present invention will be described with the conventional ABC as an example. The technique described in the third embodiment of the present invention may not be applicable to X-ray radiography.

As shown in FIG. 3, the X-ray diagnosis apparatus includes an X-ray tube 2, a transmitted X-ray detector 3, an integrator 4, and an X-ray control circuitry 100. The X-ray control circuitry 100 includes a comparator 5, a time measurement unit 6, and an X-ray condition-setting unit 1. The X-ray tube 2 radiates an X-ray towards a patient P. The transmitted X-ray detector 3 detects an X-ray transmitted through the patient P as a result of the X-ray radiation by the X-ray tube 2. The integrator 4 integrates detected results obtained from the transmitted-X-ray detector 3. The comparator 5 compares an integrated result obtained from the integrator 4 to a reference value. The reference value is usually determined, in advance, to represent an optimal brightness of an X-ray fluoroscopic image. The time measurement unit 6 generates termination signals to control the X-ray radiation time (a width of each intermittent X-ray pulse) by the X-ray tube 2, based on a comparison result obtained from the comparator 5. The time measurement unit 6 may also transfer the comparison result to the X-ray condition-setting unit 1 when the ABC is performed. The X-ray condition-setting unit 1 sets and controls X-ray conditions of the X-ray radiation by the X-ray tube 2, such as an X-ray tube voltage and an X-ray tube current. During the ABC, the X-ray condition-setting unit 1 further controls those conditions based on the comparison result obtained from the comparator 5 (through the time measurement unit 6).

Responsive to activation of an X-ray radiation switch (foot switch) by an operator, the X-ray tube 2 begins an X-ray radiation for the continuous X-ray fluoroscopy. The X-ray radiation is made with an X-ray under an X-ray tube voltage (kV) and an X-ray tube current (mA) set in advance by the X-ray condition-setting unit 1. Since the thickness of a patient body to be fluoroscoped may depend on each individual patient and also on a part of his or her body, it would be helpful to know the thickness in advance so as to guess or estimate what strength of an X-ray should be radiated from an X-ray tube in the X-ray fluoroscopy. This makes it possible to reduce a time for the ABC and also an entire fluoroscopy including the AEC, by beginning the ABC with an estimated X-ray tube voltage and an estimated X-ray tube current for the radiation mentioned above. For example, a table can be prepared with a relationship between a plurality of thickness for a human beings' body and combinations of X-ray tube voltage and X-ray tube current (or a variety of one of the X-ray tube voltage and the X-ray tube current when the other is fixed). Accordingly, it is possible to determine a set of an X-ray tube voltage and an X-ray tube current corresponding to one thickness if the one thickness is input, for example.

Responsive to the activation of the X-ray radiation, the X-ray is radiated to the patient P as shown in FIG. 7. The X-ray is detected as a transmission X-ray in the transmitted X-ray detector 3. To be more precise, the transmission X-ray is detected in the transmitted X-ray detector 3 as a result that the X-ray is transmitted through the patient P. The transmission X-ray detected in the transmitted X-ray detector 3 is fed to the comparator 5 as transmission X-ray data, through the integrator 4 which is disabled, or directly, for example, by switching to connect the transmitted-X-ray detector 3 directly with the comparator 5. The comparator 5 compares the fed transmission X-ray data to the reference value at predetermined intervals. The comparison result by the comparator 5 is sent to the X-ray condition-setting unit 1, through the time measurement unit 6, or directly, for example, by switching to connect the comparator 5 directly with the X-ray condition-setting unit 1. The X-ray condition-setting unit 1 reads the comparison result at predetermined intervals. If the X-ray condition-setting unit 1 determines that the current transmission X-ray data are too high, compared to the reference value, it controls to lower at least one of the X-ray tube voltage and the X-ray tube current. On the other hand, if the X-ray condition-setting unit 1 determines that the current transmission X-ray data are too low, compared to the reference value, it controls to raise at least one of the X-ray tube voltage and the X-ray tube current. Such a control process may be repeated until the transmission X-ray data are approximated to the reference value, by controlling at least one of the X-ray tube voltage and the X-ray tube current.

The continuous fluoroscopy described above determines an initial X-ray tube voltage and an initial X-ray tube current to be used in the AEC. The ABC may be terminated when the transmission X-ray data are approximated to or not so different from the reference value. The transmission X-ray data may not be required to be identical with the reference value. With the initial X-ray tube voltage and the initial X-ray tube current based on the transmission X-ray data obtained in the ABC, the AEC can realize a reduction of time for obtaining an optimal brightness of an X-ray fluoroscopic image.

When the ABC in the continuous X-ray fluoroscopy is over, the AEC begins. In the AEC, a first X-ray pulse (a first intermittent pulse X-ray) (a4), which is generated based on the initial X-ray tube voltage and the initial X-ray tube current obtained in the ABC, is radiated to the patient P as shown in FIG. 7. The first X-ray pulse (a4) is detected as a transmission X-ray in the transmitted X-ray detector 3. To be more precise, the transmission X-ray is detected in the transmitted X-ray detector 3 as a result that the first X-ray pulse (a4) is transmitted through the patient P. The transmission X-ray detected in the transmitted X-ray detector 3 is sent to the integrator 4. The integrator 4 continues to integrate the transmission X-ray and feeds the integrated transmission X-ray to the comparator 5 as the transmission X-ray data at predetermined intervals. The comparator 5 compares the fed transmission X-ray data to the reference value at predetermined intervals.

As already described before, the width of each intermittent X-ray pulse is not fixed but varies according to the control by the time measurement unit 6. Therefore, the radiation in the first X-ray pulse (a4) continues until terminated by the termination control by the time measurement unit 6 and, as a result, the transmission X-ray data increase as the radiation time goes by.

The comparison result by the comparator 5 is sent to the time measurement unit 6. The comparison result may, for example, be signals representing whether the transmission X-ray data have reached the reference value or not. When the timed measurement unit 6 receives such signals representing that the transmission X-ray data have not reached the reference value in spite of the elapse of the allowable maximum length of the X-ray pulse radiation time, such signals are transferred to the X-ray condition-setting unit 1. Such signals may alternatively be sent to the X-ray condition-setting unit 1 directly from the comparator 5. The X-ray condition-setting unit 1 increases or controls to adjust at least one of the X-ray tube voltage and the X-ray tube current for the second X-ray pulse (b4) so that the transmission X-ray data reach the reference value within the allowable maximum length of the X-ray pulse radiation time. Accordingly, the second X-ray pulse (b4) is radiated with a newly set condition including an increased or controlled X-ray tube voltage and/or an increased or controlled X-ray tube current.

On the other hand, if the time measurement unit 6 receives signals representing that the transmission X-ray data have exceeded the reference value only in the allowable minimum length of the X-ray pulse radiation time, such signals are transferred to the X-ray condition-setting unit 1. Such signals may alternatively be sent to the X-ray condition-setting unit 1 directly from the comparator 5. The X-ray condition-setting unit 1 decreases or controls to adjust at least one of the X-ray tube voltage and the X-ray tube current for the second X-ray pulse (b4) so that the transmission X-ray data do not exceed but reach the reference value within the allowable maximum length of the X-ray pulse radiation time. Accordingly, the second X-ray pulse (b4) is radiated with a newly set condition including a decreased or controlled X-ray tube voltage and/or a decreased or controlled X-ray tube current.

Accordingly, when the time measurement unit 6 receives signals representing that the transmission X-ray data have reached the reference value, the time measurement unit 6 sends termination signals to the X-ray tube 2 so that the X-ray tube 2 terminates its X-ray radiation. Once the X-ray radiation is terminated, the X-ray is not radiated until a time for a third X-ray pulse (c4). The AEC process described above may be repeated in each of the following X-ray pulses, such as X-ray pulses (c4), and (d4), in a similar manner. This results in producing X-ray fluoroscopic images with an optimal brightness.

According to the third embodiment of the present invention, however, the first X-ray pulse (a4) is generated with the initial X-ray tube voltage and the initial X-ray tube current obtained in the ABC. Therefore, it may be likely that the transmission X-ray data reach the reference value in the first X-ray pulse (a4). Further, it would not take an unnecessarily long time even during the first X-ray pulse (a4) for the transmission X-ray data to reach the reference value. Therefore, it may be possible to obtain the optimal and stable brightness of an X-ray fluoroscopic image more quickly than according to the first and second embodiments of the present invention.

As described above, in the X-ray diagnosis apparatus according to the third embodiment of the present invention, in order to obtain an optimal brightness of an X-ray fluoroscopic image, the continuous X-ray fluoroscopy is implemented first so as to guess or determine an appropriate initial X-ray tube voltage and an appropriate initial X-ray tube current for the first intermittent X-ray pulse in the AEC. The AEC can be initiated with the initial X-ray tube voltage and the initial X-ray tube current. Therefore, even at a low rate of intermittent X-ray pulse radiation, it may be possible to obtain the optimal brightness of an X-ray fluoroscopic image quickly. For example, the optimal brightness may be expected to be obtained in a period on the order of tens of milliseconds.

(Fourth Embodiment)

Figure 8:
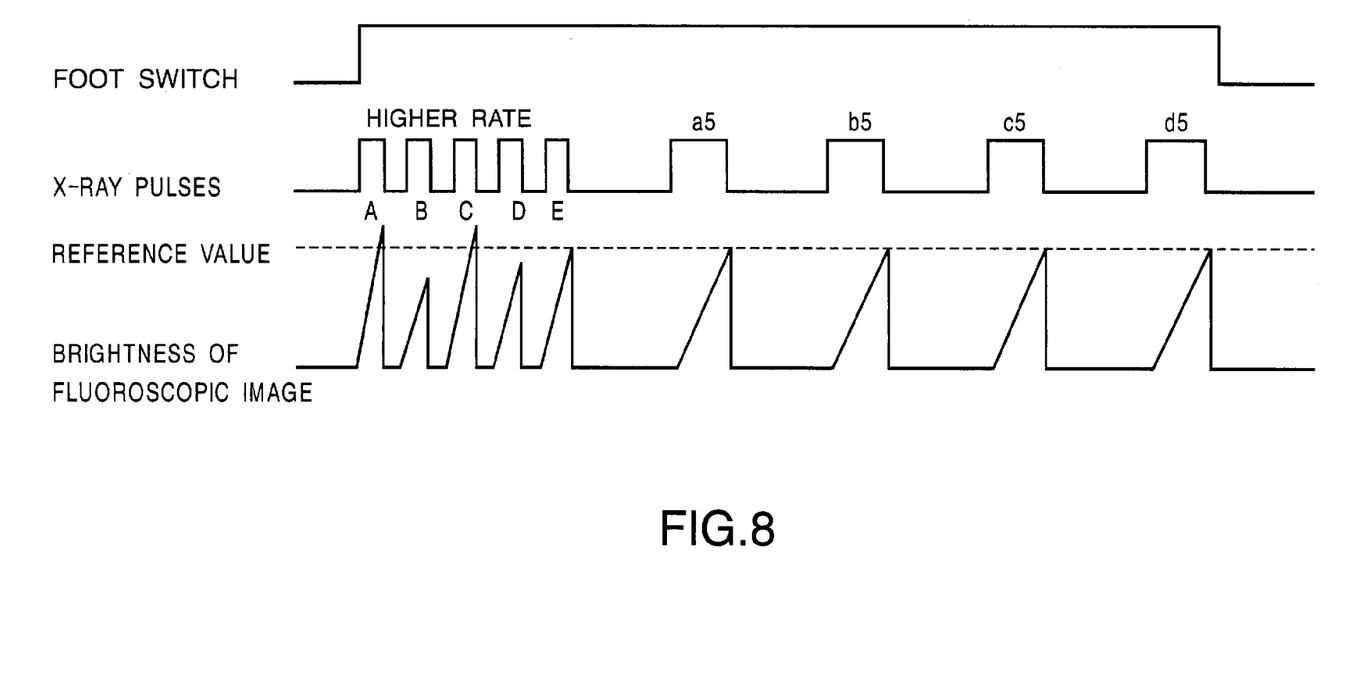
FIG. 8 is a diagram showing another process for obtaining an optimal or preferable brightness of the X-ray fluoroscopic image in the X-ray diagnosis apparatus according to the present invention.

A configuration of an X-ray diagnosis apparatus according to a fourth embodiment of the present invention will be explained with reference to FIG. 3 again. Further, FIG. 8 is a diagram showing another process for obtaining an optimal brightness of an X-ray fluoroscopic image in the X-ray diagnosis apparatus according to the fourth embodiment of the present invention. In the X-ray diagnosis apparatus according to the fourth embodiment of the present invention, an X-ray fluoroscopy with an X-ray pulsed at a higher rate than at a rate for the AEC is implemented in advance of the AEC, such as, but not limited to, those described in the first and the second embodiments of the present invention. Accordingly, an initial X-ray tube voltage and/or an initial X-ray tube current for the AEC may be determined based on a result of the advance higher rate pulse X-ray fluoroscopy. The higher rate pulse X-ray fluoroscopy may be performed with either the conventional ABC in a pulse fluoroscopy or a technique using a concept of the AEC. The fourth embodiment of the present invention will be described with the conventional ABC as an example. The technique described in the fourth embodiment of the present invention may not be applicable to X-ray radiography.

As shown in FIG. 3, the X-ray diagnosis apparatus includes an X-ray tube 2, a transmitted X-ray detector 3, an integrator 4, and an X-ray control circuitry 100. The X-ray control circuitry 100 includes a comparator 5, a time measurement unit 6, and an X-ray condition-setting unit 1. The X-ray tube 2 radiates an X-ray towards a patient P. The transmitted X-ray detector 3 detects an X-ray transmitted through the patient P as a result of the X-ray radiation by the X-ray tube 2. The integrator 4 integrates detected results obtained from the transmitted X-ray detector 3. The comparator 5 compares an integrated result obtained from the integrator 4 to a reference value. The reference value is usually determined, in advance, to represent an optimal brightness of an X-ray fluoroscopic image. The time measurement unit 6 generates termination signals to control the X-ray radiation time (a width of each intermittent X-ray pulse) by the X-ray tube 2, based on a comparison result obtained from the comparator 5. The time measurement unit 6 may also transfer the comparison result to the X-ray condition-setting unit 1 when the ABC is performed. The X-ray condition-setting unit 1 sets and controls X-ray conditions of the X-ray radiation by the X-ray tube 2, such as an X-ray tube voltage and an X-ray tube current. During the ABC, the X-ray condition-setting unit 1 further controls those conditions based on the comparison result obtained from the comparator 5 (through the time measurement unit 6).

Responsive to activation of an X-ray radiation switch (foot switch) by an operator, the X-ray tube 2 begins an X-ray radiation in a form of pulses at a higher rate for the ABC than at a rate for the following AEC. The X-ray radiation is made with the intermittent pulse X-ray.

Similar to the prior art, first of all, a first X-ray pulse (a first intermittent pulse X-ray) (A) is radiated to the patient P as shown in FIG. 8. The first X-ray pulse (A) is detected in the transmitted-X-ray detector 3 and integrated in the integrator 4 as integrated X-ray data. The integrated X-ray data are fed back to the comparator 5. In the comparator 5, the integrated X-ray data are compared to the reference value. The comparison result is fed to the X-ray condition-setting unit 1 directly or through the time measurement unit 6. The X-ray condition-setting unit 1 determines a condition of a next X-ray pulse according to the comparison result and sets a determined condition for the X-ray tube 2. The condition to be determined includes, for example, an X-ray tube voltage and an X-ray tube current of the X-ray pulse. Under the set condition, a second X-ray pulse (a second intermittent pulse X-ray) (B) is radiated to the patient P and a similar brightness control is performed as described above. By repeating such brightness control processes in the following X-ray pulses (C), (D), and (E), the transmission X-ray data are approximated to the reference value.

The higher rate pulse X-ray fluoroscopy described above determines an initial X-ray tube voltage and an initial X-ray tube current to be used in the AEC. The ABC may be terminated when the transmission X-ray data are approximated to or not so different from the reference value. The transmission X-ray data may not be required to be identical with the reference value. With the initial X-ray tube voltage and the initial X-ray tube current based on the transmission X-ray data obtained in the ABC, the ABC can realize reduction of time for obtaining an optimal brightness of an X-ray fluoroscopic image.

When the ABC in the higher rate pulse X-ray fluoroscopy is over, the AEC begins. In the AEC, a first X-ray pulse (a first intermittent pulse X-ray) (a5), which is generated based on the initial X-ray tube voltage and the initial X-ray tube current obtained in the ABC, is radiated to the patient P as shown in FIG. 8. The first X-ray pulse (a5) is detected as a transmission X-ray in the transmitted X-ray detector 3. To be more precise, the transmission X-ray is detected in the transmitted X-ray detector 3 as a result that the first X-ray pulse (a5) is transmitted through the patient P. The transmission X-ray detected in the transmitted X-ray detector 3 is sent to the integrator 4. The integrator 4 continues to integrate the transmission X-ray and feeds the integrated transmission X-ray to the comparator 5 as transmission X-ray data at predetermined intervals. The comparator 5 compares the fed transmission X-ray data to the reference value at predetermined intervals.

As already described before, the width of each intermittent X-ray pulse is not fixed but varies according to the control by the time measurement unit 6. Therefore, the radiation in the first X-ray pulse (a5) continues until terminated by the termination control by the time measurement unit 6 and, as a result, the transmission X-ray data increase as the radiation time goes by.

The comparison result by the comparator 5 is sent to the time measurement unit 6. The comparison result may, for example, be signals representing whether the transmission X-ray data have reached the reference value or not. When the time measurement unit 6 receives such signals representing that the transmission X-ray data have not reached the reference value in spite of the elapse of the allowable maximum length of the X-ray pulse radiation time, such signals are transferred to the X-ray condition-setting unit 1. Such signals may alternatively be sent to the X-ray condition-setting unit 1 directly from the comparator 5. The X-ray condition-setting unit 1 increases or controls to adjust at least one of the X-ray tube voltage and the X-ray tube current for the second X-ray pulse (b5) so that the transmission X-ray data reach the reference value within the allowable maximum length of the X-ray pulse radiation time. Accordingly, the second X-ray pulse (b5) is radiated with a newly set condition including an increased or controlled X-ray tube voltage and/or an increased or controlled X-ray tube current.

On the other hand, if the time measurement unit 6 receives signals representing that the transmission X-ray data have exceeded the reference value only in the allowable minimum length of the X-ray pulse radiation time, such signals are transferred to the X-ray condition-setting unit 1. Such signals may alternatively be sent to the X-ray condition-setting unit 1 directly from the comparator 5. The X-ray condition-setting unit 1 decreases or controls to adjust at least one of the X-ray tube voltage and the X-ray tube current for the second X-ray pulse (b5) so that the transmission X-ray data do not exceed but reach the reference value within the allowable maximum length of the X-ray pulse radiation time. Accordingly, the second X-ray pulse (b5) is radiated with a newly set condition including a decreased or controlled X-ray tube voltage and/or a decreased or controlled X-ray tube current.

Accordingly, when the time measurement unit 6 receives signals representing that the transmission X-ray data have reached the reference value, the time measurement unit 6 sends termination signals to the X-ray tube 2 so that the X-ray tube 2 terminates its X-ray radiation. Once the X-ray radiation is terminated, the X-ray is not radiated until a time for a third X-ray pulse (c5). The AEC process described above may be repeated in each of the following X-ray pulses, such as X-ray pulses (c5) and (d5), in a similar manner. This results in producing X-ray fluoroscopic images with an optimal brightness.

According to the fourth embodiment of the present invention, however, the first X-ray pulse (a5) is generated with the initial X-ray tube voltage and the initial X-ray tube current obtained in the ABC. Therefore, it may be likely that the transmission X-ray data reach the reference value in the first X-ray pulse (a5). Further, it would not take an unnecessarily long time even during the first X-ray pulse (a5) for the transmission X-ray data to reach the reference value. Therefore, it may be possible to obtain the optimal and maybe stable brightness of an X-ray fluoroscopic image more quickly than according to the first and second embodiments of the present invention.

As described above, in the X-ray diagnosis apparatus according to the fourth embodiment of the present invention, in order to obtain an optimal brightness of an X-ray fluoroscopic image, the higher rate pulse X-ray fluoroscopy is implemented first so as to estimate or determine an appropriate initial X-ray tube voltage and an appropriate initial X-ray tube current for the first intermittent X-ray pulse in the AEC. The AEC can be initiated with the initial X-ray tube voltage and the initial X-ray tube current. Therefore, even at a low rate of intermittent X-ray pulse radiation, it may be possible to obtain the optimal brightness of an X-ray fluoroscopic image quickly.

In the embodiments of the present invention, the X-ray diagnosis apparatus may have a random access memory (RAM), which can receive and store computer programs and applications as computer readable instructions in a temporary and/or non-volatile state. The X-ray diagnosis apparatus may further have a hard disk drive for reading from and writing to a hard disk, a magnetic disk drive for reading from and writing to a magnetic disk, and/or an optical disk drive for reading from and writing to an optical disk (such as for example a CD-ROM, magneto-optical disks, ROMs, RAMs, EPROMs, EEPROMs, Flash Memory, Magnetic or Optical Cards, DVD or any type of media suitable for storing electronic instructions). Those skilled in the art will appreciate that one or more of such memory, drives, and their respective media are examples of a computer program product for storing computer readable instructions, which when executed, may implement an embodiment of the present invention.

This invention may also be conveniently implemented using a conventional general purpose digital computer programmed according to the teachings of the present specification, as will be apparent to those skilled in the computer art. Appropriate software coding can readily be prepared by skilled programmers based on the teachings of the present disclosure as will be apparent to those skilled in the software art. In particular, the computer program product controlling the operation of the X-ray fluoroscopy apparatus of the present invention can be written in a number of computer languages including but not limited to C, C++, Fortran, and Basic, as would be recognized by those of ordinary skill in the art. The invention may also be implemented by the preparation of applications specific integrated circuits or by interconnecting an appropriate network of conventional component circuits, as will be readily apparent to those skilled in the art.

The embodiments of the present invention described above are examples described only for making it easier to understand the present invention, and are not described for the limitation of the present invention. Consequently, each component and element disclosed in the embodiments of the present invention may be redesigned or modified to its equivalent within a scope of the present invention.

Numerous modifications and variations of the present invention are possible in light of the above teachings. It is therefore understood that within the scope of the appended claims, the invention can be practiced otherwise than as specifically described.

What is claimed is:

1. An apparatus for X-ray fluoroscopy, comprising:
   a generator configured to generate X-rays for the X-ray fluoroscopy; a detector configured to detect transmission of the X-rays transmitted through an object of the X-ray fluoroscopy; an X-ray control unit configured to control the generator to generate a series of several pulses of the X-ray including a first pulse to establish at least one of an initial voltage and an initial current of the X-ray and to generate a second pulse having a shorter duration than the first pulse, said second pulse of the X-rays generated under the at least one of the initial voltage and the initial current of the first pulse to establish a pulse width.

2. The apparatus according to claim 1, wherein the X-ray control unit is configured to control the X-ray fluoroscopy by an auto brightness control.

3. The apparatus according to claim 1, wherein the X-ray control unit is configured to control the X-ray fluoroscopy by an auto exposure control.

4. An apparatus for X-ray fluoroscopy, comprising:
   a generator configured to generate X-rays for the X-ray fluoroscopy; a detector configured to detect transmission of the X-rays transmitted through an object of the X-ray fluoroscopy; and an X-ray control unit configured to control the generator to generate a first series of several pulses of the X-rays including a first pulse at a first intermittent rate and width to determine at least one of an initial voltage and an initial current of the X-ray and also to generate a second series of several pulses of the X-rays at a second intermittent rate wherein the first rate is greater than the second rate.

5. The apparatus according to claim 4, wherein the X-ray control unit is configured to control the X-ray fluoroscopy by an auto brightness control.

6. The apparatus according to claim 4, wherein the X-ray control unit is configured to control the X-ray fluoroscopy by an auto exposure control.

7. A method for producing an X-ray fluoroscopic image, comprising:
   generating X-rays for the X-ray fluoroscopy from a generator; detecting transmission of the X-rays transmitted through an object of the X-ray fluoroscopy; controlling the generator to generate a series of several pulses of the X-rays including a first pulse to establish at least one of an initial voltage and an initial current of the X-rays and to generate a second pulse having a shorter duration than the first pulse, said second pulse of the X-rays generated under the at least one of the initial voltage and the initial current of the first pulse to establish a pulse width.

8. A method for producing an X-ray fluoroscopic image, comprising:
   generating X-rays for the X-ray fluoroscopy from a generator; detecting transmission of the X-rays transmitted through an object of the X-ray fluoroscopy; controlling the generator to generate a first series of several pulses of the X-ray including a first pulse at a first intermittent rate and width to determine at least one of an initial voltage and an initial current of the X-rays; and controlling the generator to generate a second series of several pulses of the X-rays at a second intermittent rate wherein the first rate is greater than the second rate.

9. An apparatus for X-ray fluoroscopy, comprising:
   means for generating X-rays for the X-ray fluoroscopy; means for detecting transmission of the X-rays transmitted through an object of the X-ray fluoroscopy; means for controlling the means for generating to generate a series of several pulses of the X-rays including a first pulse to establish at least one of an initial voltage and an initial current of the X-rays and to generate a second pulse having a shorter duration than the first pulse, said second pulse of the X-rays generated under the at least one of the initial voltage and the initial current of the first pulse to establish a pulse width.

10. An apparatus X-ray fluoroscopy, comprising:
    means for generating X-rays for the X-ray fluoroscopy; means for detecting transmission of the X-rays transmitted through an object of the X-ray fluoroscopy; means for controlling the means for generating to generate a first series of several pulses of the X-rays including a first pulse at a first intermittent rate and width to determine at least one of an initial voltage and an initial current of the X-ray and also controlling the means for generating to generate a second series of several pulses of the X-rays, at a second intermittent rate wherein the first rate is greater than the second rate.

* * * * *